US012277651B1

(12) United States Patent
Villongco et al.

(10) Patent No.: US 12,277,651 B1
(45) Date of Patent: Apr. 15, 2025

(54) 3D CARDIAC VISUALIZATION SYSTEM

(71) Applicant: The Vektor Group Inc., San Diego, CA (US)

(72) Inventors: Christopher J. T. Villongco, Oakland, CA (US); Robert Joseph Krummen, Bellevue, WA (US); Christian David Marton, Jersey City, NJ (US)

(73) Assignee: THE VEKTOR GROUP, INC., San Diego, CA (US)

( * ) Notice: Subject to any disclaimer, the term of this patent is extended or adjusted under 35 U.S.C. 154(b) by 0 days.

(21) Appl. No.: 18/737,950

(22) Filed: Jun. 8, 2024

(51) Int. Cl.
| | |
|---|---|
| *G06T 17/20* | (2006.01) |
| *A61B 5/339* | (2021.01) |
| *G06T 7/00* | (2017.01) |
| *G06T 7/11* | (2017.01) |

(Continued)

(52) U.S. Cl.
CPC ............. *G06T 17/20* (2013.01); *A61B 5/339* (2021.01); *G06T 7/0012* (2013.01); *G06T 7/11* (2017.01); *G06T 13/20* (2013.01); *G06T 15/08* (2013.01); *G06T 2200/04* (2013.01); *G06T 2207/10016* (2013.01); *G06T 2207/30048* (2013.01); *G06T 2210/41* (2013.01)

(58) Field of Classification Search
CPC ......... G06T 17/20; G06T 7/0012; G06T 7/11; G06T 13/20; G06T 15/08; G06T 2200/04; G06T 2207/10016; G06T 2207/30048; G06T 2210/41; A61B 5/339
See application file for complete search history.

(56) References Cited

U.S. PATENT DOCUMENTS

| | | | | |
|---|---|---|---|---|
| 5,889,524 A | * | 3/1999 | Sheehan | ................. G06T 17/20 345/419 |
| 6,301,496 B1 | * | 10/2001 | Reisfeld | ................. A61B 5/287 600/407 |

(Continued)

FOREIGN PATENT DOCUMENTS

| | | |
|---|---|---|
| WO | 2021163227 A1 | 8/2021 |
| WO | 2023150644 A1 | 8/2023 |

OTHER PUBLICATIONS

Aguado-Sierra et al., "Patient-Specific Modeling of Dyssynchronous Heart Failure: A Case Study," Prog Biophys Mol Biol., Oct. 2011, 23 pages.

(Continued)

*Primary Examiner* — Motilewa Good-Johnson
(74) *Attorney, Agent, or Firm* — Perkins Coie LLP

(57) ABSTRACT

A system is provided for generating and displaying a sequence of three-dimensional (3D) graphics that illustrate motion of the heart over a cardiac cycle. The system generates a start heart wall mesh and an end heart wall mesh that represent a start geometry and an end geometry of a heart wall derived from a start 3D image and an end 3D image. The system then generates one or more an intermediate heart wall 3D meshes based on an intermediate geometry of the heart wall. An intermediate geometry is interpolated based on the start geometry and the end geometry factoring a start time of a start heart wall mesh, an end time of the end heart wall mesh, and an intermediate time for the intermediate heart wall mesh. The system then displays in sequence representations the heart wall 3D meshes to illustrate the motion.

19 Claims, 8 Drawing Sheets

(51) Int. Cl.
*G06T 13/20* (2011.01)
*G06T 15/08* (2011.01)

(56) References Cited

U.S. PATENT DOCUMENTS

| | | | |
|---|---|---|---|
| 7,043,062 B2* | 5/2006 | Gerard | G06T 17/00 382/128 |
| 10,448,901 B2 | 10/2019 | McVeigh et al. | |
| 11,250,628 B2* | 2/2022 | Su | G06T 7/0012 |
| 11,896,432 B2* | 2/2024 | Villongco | A61B 8/0883 |
| 2003/0160786 A1* | 8/2003 | Johnson | G06T 17/20 345/419 |
| 2008/0137929 A1* | 6/2008 | Chen | G06T 17/20 382/131 |
| 2008/0317308 A1* | 12/2008 | Wu | G06T 7/0012 382/128 |
| 2009/0136103 A1* | 5/2009 | Sonka | G06V 10/7635 382/128 |
| 2016/0379372 A1* | 12/2016 | Groth | G06T 7/149 382/131 |
| 2019/0333643 A1* | 10/2019 | Villongco | G06V 10/764 |
| 2022/0047868 A1* | 2/2022 | Odland | A61N 1/0502 |
| 2022/0175295 A1* | 6/2022 | Montag | A61B 5/335 |
| 2022/0370033 A1* | 11/2022 | Klingensmith | G06T 7/0012 |
| 2022/0409160 A1* | 12/2022 | Buckler | G16C 20/30 |
| 2023/0225800 A1* | 7/2023 | Grund | A61B 5/366 600/523 |
| 2024/0202919 A1* | 6/2024 | Shige | G06T 7/0012 |
| 2024/0215863 A1* | 7/2024 | Hirson | A61B 5/1075 |

OTHER PUBLICATIONS

Al-Issa et al., "Regional function analysis of left atrial appendage using motion estimation CT and risk of stroke in patients with atrial fibrillation," European Heart Journal—Cardiovascular Imaging, Jul. 2016, 9 pages.

Bruns et al., "Deep learning-based whole-heart segmentation in 4D contrast-enhanced cardiac CT," Computers in Biology and Medicine, Mar. 2022, 9 pages.

Bustamante et al., "Automatic Time-Resolved Cardiovascular Segmentation of 4D Flow MRI Using Deep Learning," J. Magn. Reson. Imaging, Jan. 2023, pp. 191-203.

Chen et al., "Myocardial Regional Shortening from 4D Cardiac CT Angiography for the Detection of Left Ventricular Segmental Wall Motion Abnormality," Radiology Cardiothoracic Imaging, Mar. 2023 March, vol. 5, No. 2-2023, 8 pages.

Fisher et al., "Multiphasic Cardiac Magnetic Resonance Imaging: Normal Regional Left Ventricular Wall Thickening," AJR Am J Roentgenol, Jul. 1985, 4 pages.

Vetter et al., "Mechanoelectric Feedback in a Model of the Passively Inflated Left Ventricle," Annals of Biomedical Engineering, vol. 29, May 2001, pp. 414-426.

Johansen et al., "The Investigation of Left Atrial Structure and Stroke Etiology: The I-LASER Study," Journal of the American Heart Association, Jan. 2021, 14 pages.

Xiao et al., "MAE-TransRNet: An improved transformer-ConvNet architecture with masked autoencoder for cardiac MRI registration," Front Med (Lausanne), Mar. 2023, 19 pages.

Wang et al., "Randomized Trial of Left Bundle Branch vs Biventricular Pacing for Cardiac Resynchronization Therapy," Journal of the American College of Cardiology, Sep. 27, 2022, 12 pages.

Ronneberger et al., "U-Net: Convolutional Networks for Biomedical Image Segmentation," Computer Science Department and BIOSS Centre for Biological Signalling Studies, University of Freiburg, Germany, May 18, 2015, 8 pages.

Qureshi et al., "Imaging and biophysical modelling of thrombogenic mechanisms in atrial fibrillation and stroke," Frontiers in Cardiovascular Medicine, Jan. 16, 2023, 14 pages.

Author Unknown, "Deep Learning Synthetic Strain: Quantitative Assessment of Regional Myocardial Wall Motion," Radiology Society of North America, 47 pages.

Prassl et al., "Automatically Generated, Anatomically Accurate Meshes for Cardiac Electrophysiology Problems," IEEE Trans Biomed Eng., May 2009 May, 37 pages.

Ouyang et al., "Video-based AI for beat-to-beat assessment of cardiac function," Nature, Apr. 2020, 19 pages.

McVeigh et al., "Regional myocardial strain measurements from 4DCT in patients with normal LV function," Journal of Cardiovascular Computed Tomography, Sep.-Oct. 2018 Sep.-Oct., pp. 372-378 (16 pages).

Liang et al., "Left Bundle Branch Pacing Versus Biventricular Pacing for Acute Cardiac Resynchronization in Patients With Heart Failure," Circulation: Arrhythmia and Electrophysiology, Nov. 2022, pp. 751-761 (11 pages).

Lee et al., "Multiresolution Mesh Morphing," Proceedings of SIGGRAPH 99, Aug. 1999, pp. 343-350 (8 pages).

Kong et al., "A deep-learning approach for direct whole-heart mesh reconstruction," Medical Image Analysis, vol. 74, 2021, 35 pages.

Chen, et al., "Detection of left ventricular wall motion abnormalities from vol. rendering of 4DCT cardiac angiograms deep learning," Frontiers in Cardiovascular Medicine, published Jul. 28, 2022, 12 pages.

* cited by examiner

3D CARDIAC VISUALIZATION SYSTEM

BACKGROUND

Imaging is an important tool for diagnosing arrhythmias and planning electrophysiological interventions. In particular, computed tomography (CT) scans and magnetic resonance imaging (MRI) scans provide anatomical and functional insights into cardiac conditions related to arrhythmias such as atrial fibrillation and ventricular tachycardia. Imaging helps electrophysiologists to precisely map the heart's electrical activity (e.g., electrical activity mapping and voltage mapping). Imaging techniques like MRI and CT provide high-resolution images that support the identification of pathways through which electrical impulses flow within the heart. By visualizing these pathways, electrophysiologists can help ensure that the interventions are accurate and effective, reducing the risk of complications. Imaging also assists in the assessment of structural heart diseases (e.g., such as cardiomyopathies or congenital heart defects) that may influence or exacerbate arrhythmias. Knowledge of these cardiac conditions helps electrophysiologists anticipate potential challenges in treatment, tailor therapies to individual needs, and monitor disease progression or treatment response over time.

Heart wall motion refers to the motion of the heart wall during contraction and expansion. Heart wall motion can provide insights into the mechanical functioning and timing of cardiac activity relative to electrical activity such as synchrony and coordination between the electrical activity and muscular contractions of the heart. Analysis of heart wall motion can be helpful in diagnosing various arrhythmic conditions such as a heart block (e.g., a second-degree atrioventricular block). Areas of delayed or diminished heart wall motion may also indicate the presence of scar tissue.

Heart wall thickness refers to the distance from the endocardium to the epicardium. Heart wall thickness affects how electrical activity travels through the heart, especially in conditions like hypertrophic cardiomyopathy. Increased heart wall thickness can lead to abnormal electrical activity such as origination of electrical activity at locations other than at the sinoatrial node. Analysis of heart wall thickness may also be helpful in the planning and execution of invasive procedures like catheter ablation. For example, during such a procedure sufficient energy needs to be delivered to transmural layers of the heart wall but not so much as to damage the heart's normal conduction system or cardiac arteries. Knowledge of heart wall thickness can help an electrophysiologist in planning a procedure such as deciding the amount of energy to use.

Heart wall strain refers to the deformation of the heart muscle during a cardiac cycle. Heart wall strain rate is the velocity of heart wall strain over a portion of the cardiac cycle. Abnormalities in heart wall strain can indicate areas of ischemia, fibrosis, or other myocardial damage that may lead to arrhythmias. Analysis of heart wall strain and heart wall strain rate may be helpful in identifying whether a patient may have an increased risk of developing an arrhythmia before it manifests clinically.

Heart wall conduction velocity refers to the speed at which electrical activity travels through the heart wall. Conduction velocity is important for maintaining the synchronous contraction and expansion of the heart. Abnormalities in conduction velocity can indicate the presence an arrhythmia. For example, in conditions like atrial fibrillation or ventricular tachycardia, understanding the conduction velocities may be helpful in designing effective ablation strategies for mitigating the effects of aberrant electrical pathways causing the arrhythmia.

Although algorithms are available to calculate heart wall values for these wall characteristics of the heart wall, the heart wall values are typically calculated only for a portion of the cardiac cycle and only for a portion of the heart. Moreover, the heart wall values may not be provided in a way that allows for a comprehensive understanding of the relationship between the different heart wall characteristics throughout a cardiac cycle. As a result, a treatment not based on such a comprehensive understanding may expose a patient to increased risk. For example, an ablation procedure may result in an initial ablation that is not effective resulting in a need for an additional ablation and a longer procedure time. Both the initial ablation and the longer procedure time exposes the patient to increased risk of an adverse outcome.

DETAILED DESCRIPTION

Figure 1:
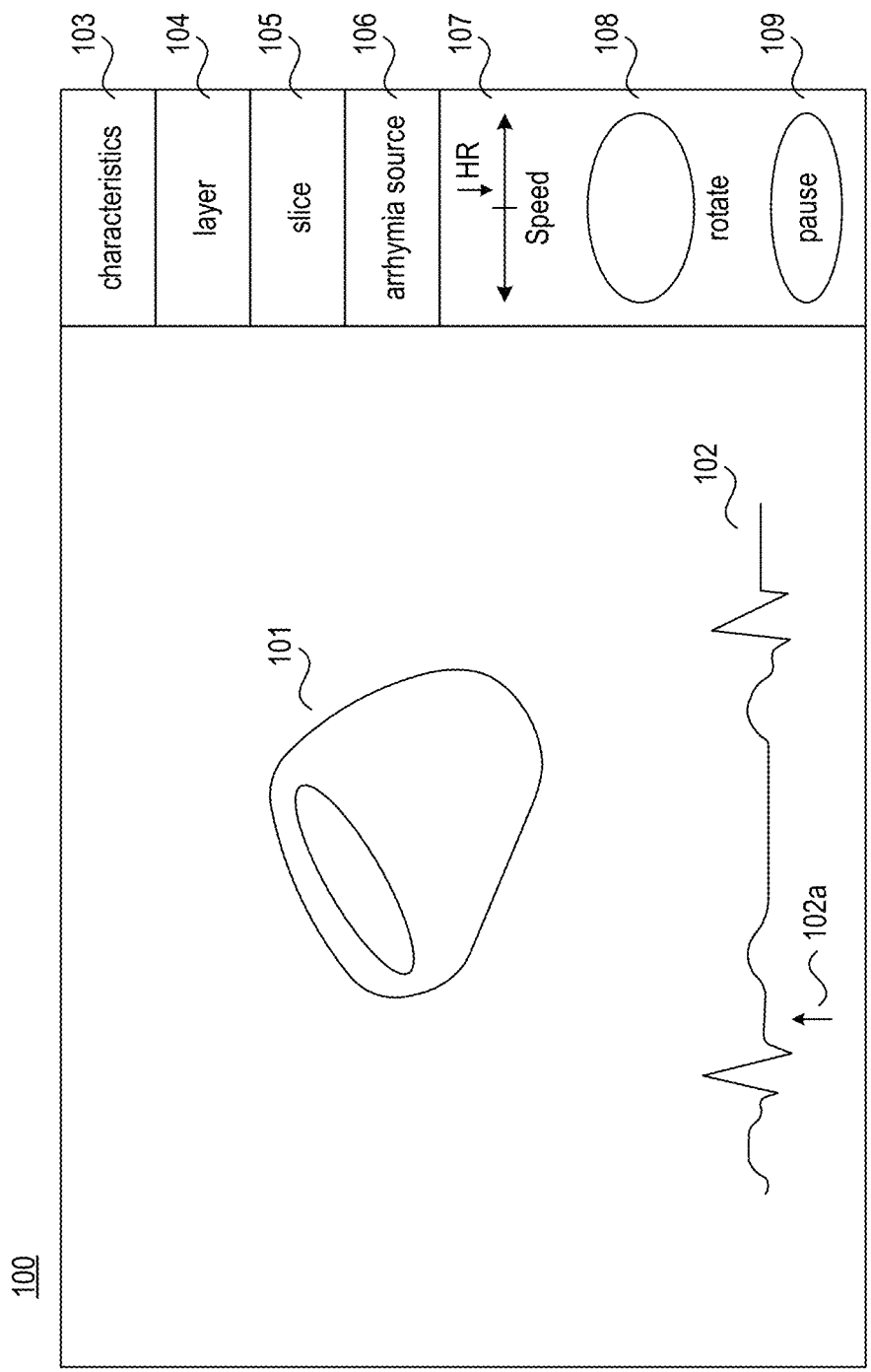
FIG. 1 is diagram that illustrates the display of a 3D graphic of a heart.

Methods and systems are provided to help inform treatment of a patient based on visualization of an organ. In some embodiments, a three-dimensional (3D) visualization system is described that provides 3D graphics of an organ along with information on characteristics relating to the organ. The organ may be, for example, a heart, a blood vessel, a gastrointestinal tract, a lung, and so on. The 3D visualization system is described primarily in the context of a heart, but the techniques described may be used in analogous manner for other organs.

In some embodiments, the 3D visualization system provides a user interface for displaying a sequence of 3D graphics representing the heart of a patient. The sequence of 3D graphics provides an animation of the motion of the heart during a portion of a cardiac cycle or during one or more cardiac cycles. The 3D visualization system accesses 3D images (e.g., CT images or MRI images) of the heart of a patient that are collected during a cardiac cycle also referred to as a heartbeat (e.g., an R-R interval covering systole and diastole). The 3D visualization system generates a segmentation of each 3D image. The segmentation demarcates structures of the heart including the inner layer (e.g., endocardium) and the outer layer (e.g., epicardium) of the heart wall, for example, of the left ventricle. The endocardium of the septum of a chamber may be considered to be the outer layer of the adjacent chamber. The 3D visualization system generates, based on the segmentation, an initial 3D mesh for each 3D image. As used in this description, the term 3D mesh refers a mesh that is collection of vertices, edges, and faces or a point cloud that is a collection of vertices. An initial 3D mesh is based on the cardiac geometry represented by the segmentation. The cardiac geometry is represented by vertices that are each associated with a location in 3D space on the inner and outer layers of the heart wall. Since the 3D meshes are generated independently, the initial 3D meshes may not have the same number of vertices. In such a case, the 3D visualization system, for each initial 3D mesh, may morph a template 3D mesh into the geometry of that initial 3D mesh to generate a morphed 3D mesh. The morphed 3D meshes have the same number of vertices which, although not necessary, simplifies subsequent processing by the 3D visualization system. In the following the term "3D mesh" refers to an initial 3D mesh or if a template mesh is morphed, the morphed 3D mesh.

After the initial 3D meshes are generated, the 3D visualization system designates a start 3D mesh associated with a start time and an end 3D mesh associated with an end time. The start time and end time may be selected based on the times at which a start 3D image and an end 3D image were collected during a cardiac cycle. The 3D visualization system may associate with vertices of the start 3D mesh and the end 3D mesh characteristic values of the wall characteristics of a patient's heart wall. The wall characteristics may be heart wall thickness, heart wall strain, heart wall conduction velocity, tissue state (e.g., viable, stunned, hibernating, and non-viable), source location of an arrhythmia source (i.e., origin), and so on. Techniques for determining tissue state are described in U.S. Pat. No. 11,896,432 titled "Machine Learning for Identifying Characteristics of a Reentrant Circuit" and issued on Feb. 13, 2024, which is hereby incorporate reference.

The 3D visualization system generates one or more intermediate 3D meshes with geometries that are based on an interpolation of the start geometry of the start 3D mesh and the end geometry of the end 3D mesh. Each intermediate 3D mesh is associated with an intermediate time that is between the start time and the end time. The interpolation may factor in a chamber volume associated with the intermediate time that may be based on mappings of a voltage-time series (e.g., electrocardiogram) or a pressure-time series to chamber volume. The pressure is a chamber pressure, such as ventricular pressure, which may be measured using a catheter during a procedure. A start chamber volume and an end chamber volume may be based on the start geometry and the end geometry, respectively. The 3D visualization system also associates characteristic values with vertices of the intermediate 3D meshes based on an interpolation of wall characteristics of the start 3D mesh and the end 3D mesh. The 3D visualization system generates a 3D graphic for each 3D mesh and displays the 3D graphics in a time-ordered sequence. Each 3D graphic includes indications of characteristic values of the corresponding 3D mesh. The characteristic values may be indicated by different colors, for example, such as shades of red, blue, and green indicating thick, normal, and thin heart wall thickness.

The 3D visualization system may employ a wall characteristics machine learning (ML) model or wall characteristics algorithm (non-ML) to determine wall characteristics based on analysis of the vertices of 3D meshes. The wall characteristics may be calculated at various times such as at maximum contraction or based on differences in cardiac geometry at maximum expansion and maximum contraction. A wall characteristics algorithm determines wall characteristics based on the locations associated with the vertices. The 3D visualization system may associate wall thickness with vertices of the inner layer of a 3D mesh. The wall thickness may be based on the distance between a vertex of the inner layer and the closest vertex of the outer layer or the closest vertex of outer layer in a specified direction (e.g., x-y plane or radially from a point within a chamber) at maximum contraction of a cardiac chamber. The search for the closest vertex of the outer layer may employ a spatial decomposition tree (SD-tree). An SD-tree organizes data by recursively subdividing the space into regions and storing information about these subdivisions. Each node in the SD-tree represents a region of space, and the leaves correspond to locations associated with vertices of the inner layer and the outer layer. Another algorithm for determining wall thickness is described in Augusto, J. B., Davies, R. H., Bhuva, A. N., Knott, K. D., Seraphim, A., Alfarih, M., Lau, C., Hughes, R. K., Lopes, L. R., Shiwani, H. and Treibel, T. A., 2021. Diagnosis and risk stratification in hypertrophic cardiomyopathy using machine learning wall thickness measurement: a comparison with human test-retest performance. The Lancet Digital Health, 3(1), pp. e20-e28, which is hereby incorporated by reference.

The wall characteristics algorithm may calculate wall motion associated with vertices of the inner layer. The wall motion of a vertex of the inner layer may be based on the distance between that vertex at maximum contraction and maximum expansion. Various techniques may be employed to determine wall motion based on analysis of 3D meshes representing the cardiac geometry over time. Such techniques are described in Yang, D., Wu, P., Tan, C., Pohl, K. M., Axel, L. and Metaxas, D., 2017. 3D motion modeling and reconstruction of left ventricle wall in cardiac MRI. In Functional Imaging and Modelling of the Heart: 9th International Conference, FIMH 2017, Toronto, ON, Canada, Jun. 11-13, 2017, Proceedings 9 (pp. 481-492). Springer International Publishing and described in Yousefi-Banaem, H., Asiaei, S. and Sanei, H., 2017. Prediction of myocardial infarction by assessing regional cardiac wall in CMR images through active mesh modeling. Computers in Biology and Medicine, 80, pp. 56-64, which are hereby incorporated by reference.

The wall characteristics algorithm may calculate wall strain for pairs of locations within the heart wall. The wall characteristics algorithm may calculate wall strain for every vertex or only for vertices corresponding to certain locations such as the inner layer, myocardial midline, and outer layer. The wall strain for a pair of vertices may be based on the difference in their locations at the maximum contraction and maximum expansion divided by the difference in their locations at maximum expansion (or at stages of the cardiac cycle other than maximum contraction and maximum expansion). Various types of wall strain measurements can be made such as longitudinal strain, radial strain, and circumferential strain. The longitudinal strain is based on the difference in length of the heart over time. The longitudinal strain may be calculated by calculating the difference in the length of the ventricles at maximum expansion and at maximum contraction and dividing the difference by the length at maximum expansion. Radial strain is based on difference in heart wall thickness over time. The radial strain may be calculated by calculating the difference in maximum expansion wall thickness and maximum contraction wall thickness measured in the x-y plane and dividing the difference by the maximum expansion wall thickness. The x-y plane is a horizontal plane. Circumferential strain is based on the difference in the circumference of the heart over time.

The circumferential strain may be calculated based on calculating the difference in maximum expansion circumference and maximum contraction circumference measured in the x-y plane and dividing that difference by the maximum expansion circumference. In addition, a strain rate can be calculated for various periods within a cardiac cycle such as for a vertex of the myocardial midline based on maximum contraction and expansion of a ventricle. The strain rate is the derivative of strain with respect to time. The derivative is calculated based on calculating a difference in a certain direction at two points in the cardiac cycle and dividing that difference by the difference in time of those two points. The strain rate is a type of wall characteristics that may be used to determine tissue state. The wall characteristics can be based on various other measurements such as Cauchy strain (1D), stretch ratio, displacement field (3D), and deformation gradient. (See, Lubliner, J., 2008. Plasticity theory. Courier Corporation.)

In some embodiments, the 3D visualization system may employ various ML architectures to generate an intermediate mesh and associated wall characteristics values. For example, a mesh ML model may have an ML architecture that includes a variational autoencoder (VAE) and a neural network (NN). The encoder of the VAE inputs a 3D mesh and outputs a latent representation of that 3D mesh. The NN inputs a start latent representation of a start 3D mesh and an end latent representation of an end 3D mesh. The latent representations of the 3D meshes are generated using the encoder of the VAE. The NN also inputs a start time and start volume; an intermediate time and an intermediate volume; and an end time and end volume. The NN outputs an intermediate latent representation of an intermediate 3D mesh corresponding the intermediate time based on the start 3D mesh and the end 3D mesh. The intermediate latent representation is input to the decoder of the VAE which outputs an intermediate 3D mesh. The NN may be, for example, fully connected with 128 layers that each includes a neuron for each bit on the input. The number of layers may be varied based on the amount of computational resource available for training and desired accuracy of the output.

The mesh ML model may be trained using 3D meshes generated based on 3D images of EHRs. Each EHR may include a start 3D image and a start time, an intermediate 3D image and an intermediate time, and an end 3D image and an end time. A 3D mesh is generated for each 3D image. The VAE is trained using the 3D meshes as training data. The NN is trained using training data that includes feature vectors based on the start latent representations, the start times, and the start volumes; the intermediate times and the intermediate volumes; and the end latent representations, the end times, and end volume. Each feature vector is labeled with the corresponding intermediate latent representation. The NN may be trained using a loss function that generates a score indicating the difference between the intermediate latent representations of the training data and the intermediate latent representations output by the NN during training. The 3D visualization system may employ a gradient descent technique when learning the weights for the VAE and weight for the NN. The VAE and the NN may also be trained with a combined loss function indicating the difference between the training intermediate 3D meshes and the intermediate 3D meshes output by the mesh ML model. In such a case, an intermediate latent representation generated during training is input to the decoder to generate an intermediate 3D mesh.

To generate an intermediate 3D mesh for a patient, the 3D visualization system inputs a start 3D image and an end 3D image of the patient's heart. The 3D visualization system then generates a start 3D mesh based on the start 3D image and an end 3D mesh based on the end 3D image. The 3D visualization system inputs the start 3D mesh to the encoder to generate a start latent representation and inputs the end 3D mesh to the encoder to generate an end latent representation. The start latent representation, a start time, and a start volume; an intermediate time and an intermediate volume; and the end latent representation, an end time, and end volume are input to the NN. The NN outputs an intermediate latent vector which is input to the decoder to generate the intermediate 3D mesh.

In addition to having a location associated with each vertex of a 3D mesh, the 3D meshes that are input to the encoder of the VAE may be associated with a characteristic value of one or more wall characteristics. In such as case, the latent representations would reflect the characteristic values. In addition, the start times, the intermediate times, and the end times employed by the mesh 3D model and, more generally by the 3D visualization system, may be normalized to a percentage or fraction of the cycle length of the cardiac cycle. For example, if a cardiac cycle is one second and the start time 250 ms, the start time may be represented as 0.25.

In some embodiments, the 3D visualization system provides a sequence of the 3D graphics that represents effects of simulating the pacing of a heart. The effects of the pacing may help inform an electrophysiologist where to place the leads of a pacemaker during cardiac resynchronization therapy. The pacing may simulate the pacing during various types of cardiac resynchronization therapy. Examples of cardiac resynchronization therapy include bi-ventricular pacing, HIS-bundle pacing, and left bundle branch area pacing.

To simulate the pacing, a 3D mesh is generated based on a 3D image taken, for example, at the start of systole. Electrical, mechanical, and geometric characteristics of a heart are identified such as action potentials, fiber orientation, and chamber volume. Given the location of the pacing lead(s), the 3D visualization system runs a simulation to simulate the electrical activity of the heart tissue and during a portion of a cardiac cycle (e.g., start systole to end systole) or during one or more cardiac cycles. For each simulation interval, a 3D mesh may be generated that represents a voltage solution and cardiac geometry. The electrical activity may be effectively initiated at a location other than a pacing location. For example, a three-lead pacemaker may result in an effective activation location that is somewhere in between pacing locations. Techniques for simulating the electromechanics of a heart are described in Aguado-Sierra, J., Krishnamurthy, A., Villongco, C., Chuang, J., Howard, E., Gonzales, M. J., Omens, J., Krummen, D. E., Narayan, S., Kerckhoffs, R. C. and McCulloch, A. D., 2011. Patient-specific modeling of dyssynchronous heart failure: a case study. Progress in biophysics and molecular biology, 107(1), pp. 147-155 and described in Kerckhoffs, R. C., Healy, S. N., Usyk, T. P. and McCulloch, A. D., 2006. Computational methods for cardiac electromechanics. Proceedings of the IEEE, 94(4), pp. 769-783, which are hereby incorporated by reference.

After running a simulation, the 3D visualization system generates a 3D graphic for 3D meshes (corresponding to a simulation interval) and displays the 3D graphics in sequence. The 3D visualization system may also include on the 3D graphics an indication of the electrical activity as it spread during the depolarization and repolarization of a cardiac cycle. The 3D visualization system may also generate and display an electrocardiogram (ECG) generated from the voltage solutions. The ECG may represent a portion of a cardiac cycle such as from start systole to end systole (e.g., represented by a QRS complex) or an entire cardiac cycle. Analysis of the ECG may indicate whether the heart or a chamber has the desired synchronization. The 3D visualization system may run multiple simulations assuming different pacemaker configurations such as lead location and pulse voltage, duration, and timing. Display of the 3D graphics and the ECG of a simulation may help inform an assessment of whether a pacemaker configuration would provide the desired synchronization (e.g., timing of contraction and expansion between cardiac chambers). Techniques for evaluating the effectiveness of pacemaker configurations are described in U.S. Pro. App. No. 63/641,844 titled "Pacemaker Configuration Identification System for Cardiac Resynchronization Therapy" and filed on May 2, 2024, which is hereby incorporated by reference.

In some embodiments, the 3D visualization system may run simulations of electromechanical activity of simulated hearts having different sets of electrical, mechanical, and geometric cardiac properties. For each simulation, a simulated ECG is generated based on the voltage solutions of the simulation. Techniques for running such simulations and generating a library that maps ECGs to the corresponding simulations are described in U.S. Pat. No. 10,860,754 titled "Calibration of Simulated Cardiograms" and issued on Dec. 8, 2020, which is hereby incorporated by reference.

Given a patient's ECG and possibly cardiac properties of the heart of a patient and pacing parameters, the 3D visualization system identifies a simulation associated with a similar ECG and similar cardiac properties and pacing parameters. The similarity may be based on a similarity criterion such as Euclidean distance, cosine similarity, and coefficient similarity. The 3D visualization system then generates and displays 3D graphics based on 3D meshes of the identified simulation and displays the ECG. Since these 3D graphics may approximate the function of the heart of the patient, the computational expense of running patient-specific simulations in real time (e.g., during a pacemaker implantation procedure) could be avoided.

In some embodiments, the 3D visualization system may calculate and display various statistics based on, for example, 3D meshes, an ECG, and/or various characteristics. The statistics may be calculated for 3D meshes generated from 3D images or generated during a simulation. The statistics based on 3D meshes may include ejection fraction, stroke volume, cardiac output, end diastole volume, and so on. The statistics based on an ECG may be QRS duration, QRS area, QRS integral, and so on. The statistics based on the characteristics may include time to peak tissue velocity, wall motion score index, and so on. Another statistic is an activation time map that indicates times at which different regions of the heart are activated by electrical impulses. The activation time may be calculated from measurements collected from a patient (e.g., using surface electrodes) or from the voltage solutions of a simulation. The 3D visualization system may indicate the activation times on a 3D graphic using contour lines that connect points with the same activation time (e.g., isochrones).

FIG. 1 is diagram that illustrates the display of a 3D graphic of a heart. The display 100 illustrates a user interface that provides a 3D graphic area 101 and an ECG area 102 with timing arrow 102a. The user interface also includes a characteristics control 103, a layer control 104, a slice control 105, an arrhythmia source control 106, a speed control 107, a rotate control 108, and a pause control 109. A sequence of 3D graphics is displayed in the 3D graphics area. A voltage-time series of an ECG is displayed in the ECG area along with a timing arrow indicating the point of the ECG that corresponds to the 3D graphic that is being displayed. The timing arrowing moves left to right during display of a sequence in time order and right to left during display of a sequence in reverse-time order. In some embodiments, the 3D visualization system may allow a user to select a start time for the start 3D image and an end time for the end 3D image. For example, although not illustrated, the 3D visualization system may allow a user to indicate a start time and an end time on the ECG. Alternatively, the 3D visualization system may allow a user to indicate the start time and the end time based on selection of ECG landmarks such as a P wave and a T wave.

The characteristics control allows a user to select one or more wall characteristics (e.g., wall thickness or wall strain rate) whose characteristic values to be displayed on the 3D graphics or to select an activation time map to display on the 3D graphic. The layer control allows a user to select a layer of the heart wall to display such as the inner layer, a transmural layer, or the outer layer. The slice control allows a user to select a slice of the 3D graphic to display. The slice may be indicated by a degree from 0 to 360. For example, a slice view of the left ventricle through the frontal plane may illustrate the thickness of the heart wall through that plane. The arrhythmia source control allows a user to select a type of arrhythmia information to be displayed. The arrhythmia information may include a color-coded arrhythmia source map as described in U.S. Pat. No. 11,189,092 titled "Computational Localization of Fibrillation Sources" and issued on Nov. 30, 2021, which is hereby incorporated by reference. The speed control allows a user to control the speed (in time order or in reverse-time order) in which the 3D graphics are displayed. The "HR" arrow of the speed control points to the speed that corresponds to the heart rate represented by the ECG. The rotate control allows a user to control rotation of the 3D graphic (e.g., in layer view or in slice view) through azimuthal angles and polar angles. Alternatively, 3D visualization system may allow a user to rotate the 3D graphic using a touchscreen display. The pause control allows a user to pause and to resume the display of the 3D graphics.

Figure 2:
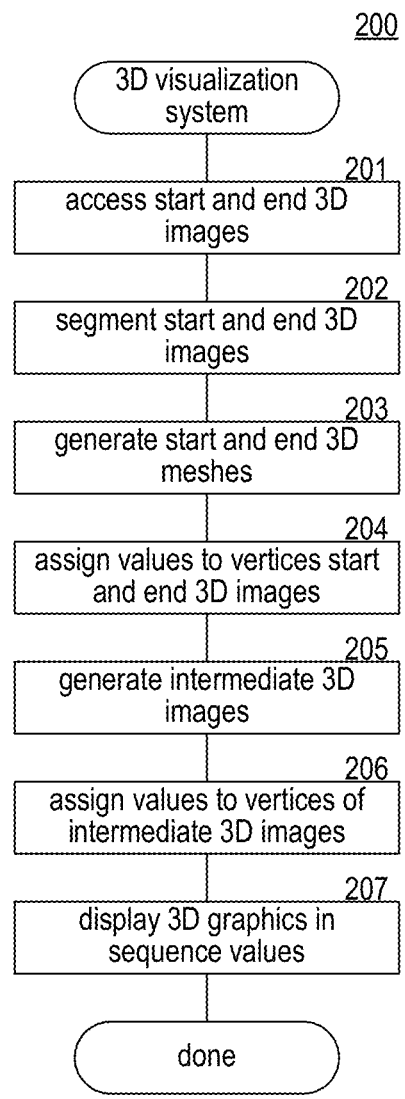
FIG. 2 is a flow diagram that illustrates the processing of the 3D visualization system in some embodiments.

FIG. 2 is a flow diagram that illustrates the processing of the 3D visualization system in some embodiments. The 3D visualization system 200 displays a sequence of 3D graphics generated from the 3D meshes corresponding to 3D images of a heart. In block 201, the system accesses a start 3D image and an end 3D image. In block 202, the system segments the start 3D image and the end 3D image. In block 203, the system generates a start 3D mesh based on the segmentation of the start 3D image and an end 3D mesh based on the segmentation of the end 3D mesh. In block 204, the system assigns characteristic values to the vertices of the start 3D mesh and the end 3D mesh. For example, the characteristic values may indicate the heart wall thickness or tissue state at a vertex representing a location on the inner layer or in the myocardium. In block 205, the system generates intermediate 3D meshes at various intermediate times based on the start 3D mesh and the end 3D mesh. In block 206, the system assigns characteristic values to the vertices of the intermediate 3D meshes. In block 207, the component displays 3D graphics generated from the 3D meshes in sequence. The 3D graphics include characteristic indicators of the characteristic values associated vertices of the 3D meshes.

Figure 3:
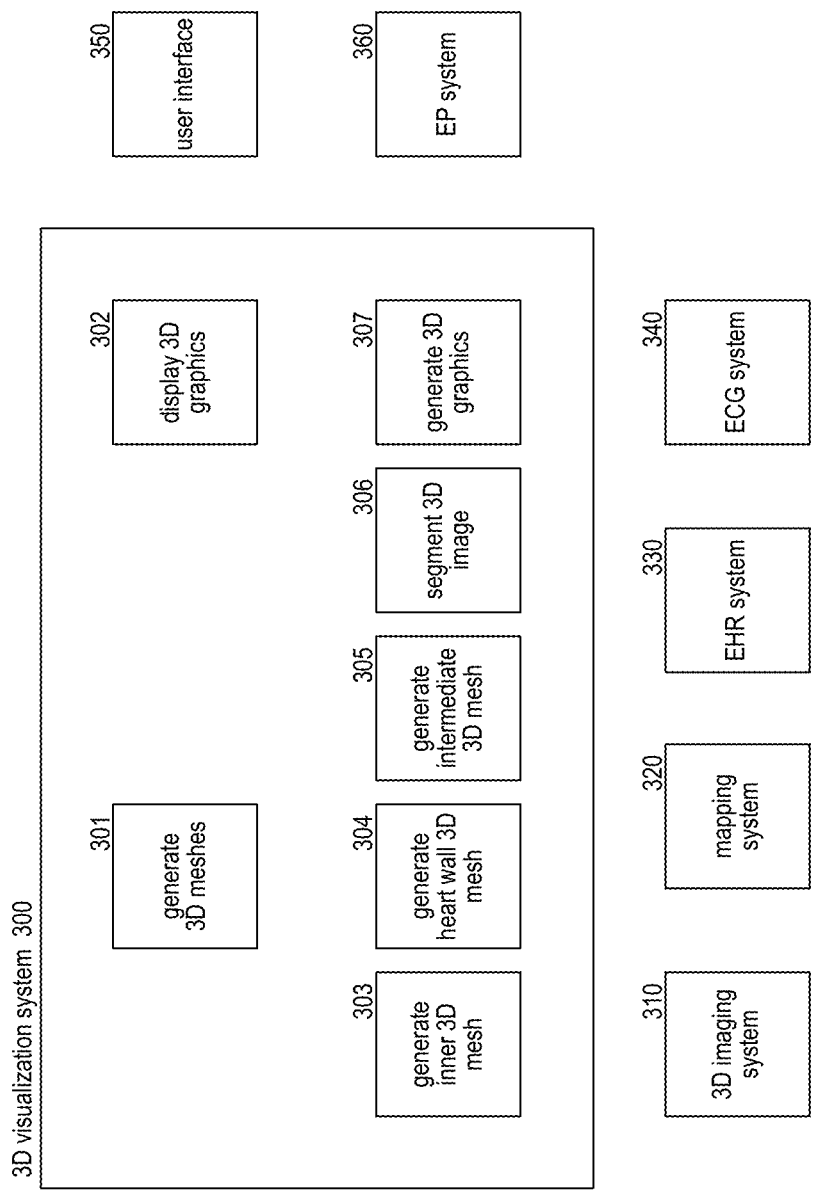
FIG. 3 is a block diagram that illustrates components of the 3D visualization system in some embodiments.

FIG. 3 is a block diagram that illustrates components of the 3D visualization system in some embodiments. The 3D visualization system 300 includes a generate 3D meshes component 301, a display 3D graphics in sequence component 302, a generate inner 3D mesh component 303, a generate heart wall 3D mesh component 304, a generate intermediate 3D mesh component 305, a segment 3D image component 306, and a generate 3D graphics component 307. The 3D visualization system interfaces with a 3D imaging system 310, a mapping system 320, an EHR system 330, an ECG system 340, a user interface system 350, and an electrophysiology system 360 (e.g., a stereotactic ablative body radiotherapy (SABR) system). The generate 3D meshes component invokes the segment 3D image component to generate a segmentation of a 3D image, the generate inner 3D mesh component to generate an inner 3D mesh based on a 3D segmentation, the generate heart wall 3D mesh component to generate a heart wall 3D mesh based on a 3D segmentation, and the generate intermediate 3D mesh component to generate an intermediate 3D mesh based on a start 3D mesh and an end 3D mesh. The display 3D graphics component invokes the generate 3D graphics component to generate a sequence of 3D graphics based on a start 3D mesh, intermediate 3D meshes, and an end 3D mesh and then displays the 3D graphics in sequence. The 3D visualization system interfaces with the 3D imaging system to acquire 3D images, the mapping system to identify wall characteristics (e.g., source location) based on an ECG, the EHR system to access characteristics of the patient (e.g., prior ablation location), the ECG system to retrieve an ECG collected from a patient, and the user interface system to display the 3D graphics and input of user commands. A mapping system is described in U.S. Pat. No. 10,856,816 titled "Machine Learning using Simulated Cardiograms" and issued on Dec. 8, 2020, which is hereby incorporated by reference.

The computing systems (e.g., network nodes or collections of network nodes) on which the 3D visualization system and the other described systems may be implemented may include a central processing unit, input devices, output devices (e.g., display devices and speakers), storage devices (e.g., memory and disk drives), network interfaces, graphics processing units, communications links (e.g., Ethernet, Wi-Fi, cellular, and Bluetooth), and so on. The input devices may include keyboards, pointing devices, touch screens, gesture recognition devices (e.g., for air gestures to rotate a 3D graphic), an augmented reality device (e.g., view the user interface during a medical procedure), head and eye tracking devices (e.g., to input selection of a user interface button), microphones for voice recognition (e.g., to input selection of user interface buttons), and so on. The computing systems may include high-performance computing systems, distributed systems, cloud-based computing systems, client computing systems that interact with cloud-based computing systems, desktop computers, laptops, tablets, e-readers, personal digital assistants, smartphones, gaming devices, servers, and so on. The computing systems may access computer-readable media that include computer-readable storage mediums and data transmission mediums. The computer-readable storage mediums are tangible storage means that do not include a transitory, propagating signal. Examples of computer-readable storage mediums include memory such as primary memory, cache memory, and secondary memory (e.g., DVD), and other storage. The computer-readable storage media may have recorded on them or may be encoded with computer-executable instructions or logic that implements the 3D visualization system and the other described systems. The data transmission media are used for transmitting data via transitory, propagating signals or carrier waves (e.g., electromagnetism) via a wired or wireless connection. The computing systems may include a secure crypto processor as part of a central processing unit (e.g., Intel Secure Guard Extension (SGX)) for generating and securely storing keys, for encrypting and decrypting data using the keys, and for securely executing all or some of the computer-executable instructions of the 3D visualization system. Some of the data (e.g., EHRs) sent by and received by the 3D visualization system may be encrypted, for example, to preserve patient privacy (e.g., to comply with government regulations such the European General Data Protection Regulation (GDPR) or the Health Insurance Portability and Accountability Act (HIPAA) of the United States). The 3D visualization system may employ asymmetric encryption (e.g., using private and public keys of the Rivest-Shamir-Adleman (RSA) standard) or symmetric encryption (e.g., using a symmetric key of the Advanced Encryption Standard (AES)).

The one or more computing systems may include client-side computing systems and cloud-based computing systems (e.g., public or private) that each executes computer-executable instructions of the 3D visualization system. A client-side computing system may send data to and receive data from one or more servers of the cloud-based computing systems of one or more cloud data centers. For example, a client-side computing system may send a request to a cloud-based computing system to generate a sequence of 3D graphics given a start 3D image and an end 3D image. A cloud-based computing system may respond to the request by sending to the client-side computing system the sequence of 3D graphics. The servers may perform computationally expensive tasks in advance of processing by a client-side computing system such as training an ML model or in response to data received from a client-side computing system. A client-side computing system may provide a user experience (e.g., user interface) to a user of the 3D visualization system. The user experience may originate from a client computing device or a server computing device. For example, a client computing device may generate a 3D graphic of a heart and display that 3D graphic. Alternatively, a cloud-based computing system may generate the 3D graphic (e.g., in a Hyper-Text Markup Language (HTML) format or an extensible Markup Language (XML) format) and provide it to the client-side computing system for display. A client-side computing system may also send data to and receive data from various medical systems such as the 3D imaging system, the mapping system, the EHR system, and the ECG system, and so on. The data received from the medical systems may include 3D images, ECGs, and so on. The data sent to a medical device may include, for example, data in a Digital Imaging and Communications in Medicine (DICOM) format that is sent to the EHR system. The term cloud-based computing system may encompass computing systems of a public cloud data center provided by a cloud provider (e.g., Azure provided by Microsoft Corporation) or computing systems of a private server farm (e.g., operated by the provider of the 3D visualization system).

The 3D visualization system and the other described systems may be described in the general context of computer-executable instructions, such as program modules and components, executed by one or more computers, processors, or other devices. Generally, program modules or components include routines, programs, objects, data structures, and so on that perform tasks or implement data types of the 3D visualization system and the other described systems. Typically, the functionality of the program modules may be combined or distributed as desired in various examples.

Figure 4:
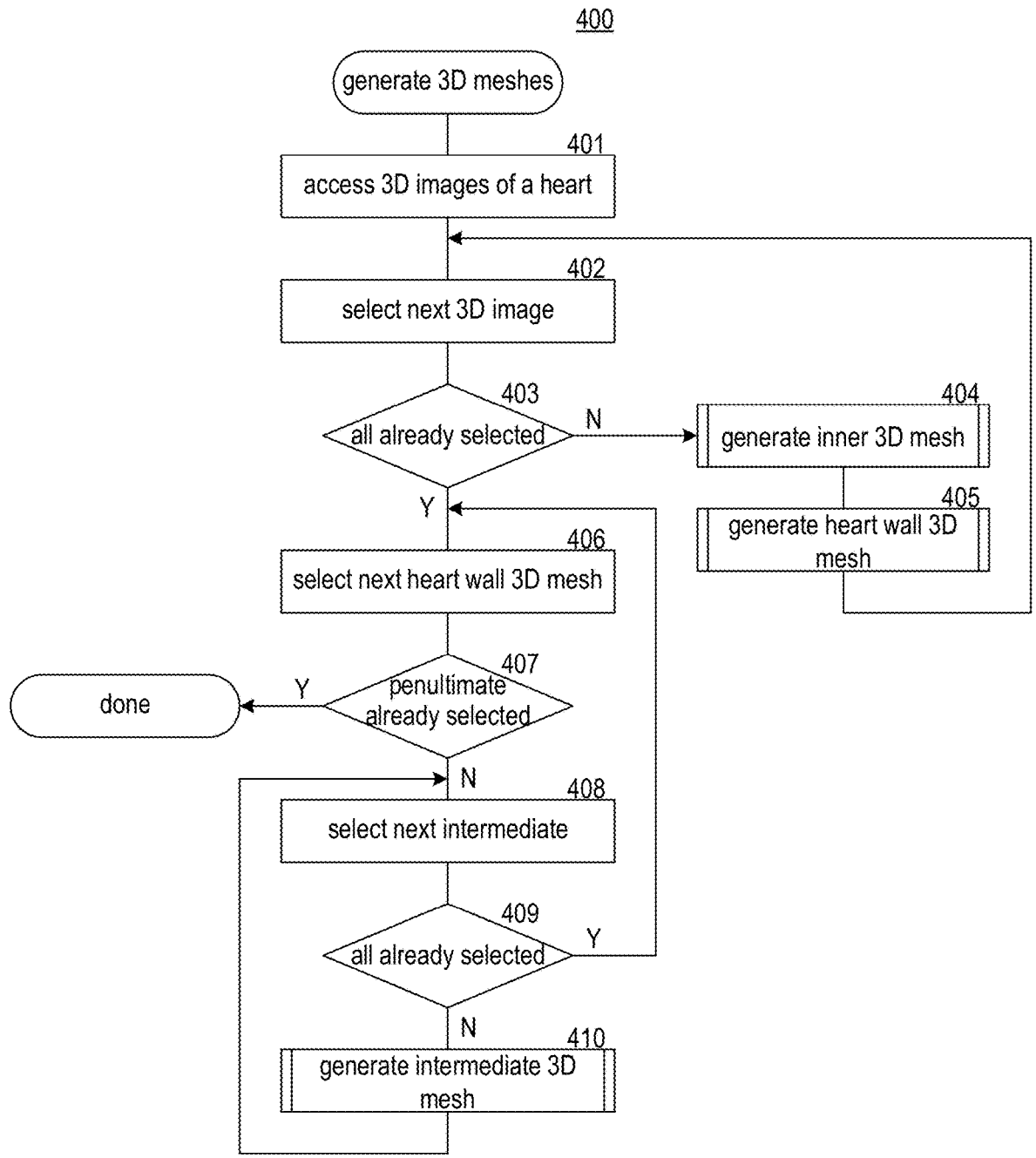
FIG. 4 is a flow diagram that illustrates the processing of the generate 3D meshes component of the 3D visualization system in some embodiments.

FIG. 4 is a flow diagram that illustrates the processing of the generate 3D meshes component of the 3D visualization system in some embodiments. The generate 3D meshes component 400 controls the generation of a sequence of 3D meshes of the heart. In block 401, the component accesses 3D images of the heart, such as a start 3D image and an end 3D image, by interfacing, for example, with the 3D imaging system or the EHR system. In block 402, the component selects the next 3D image. In decision block 403, if all the 3D images have already been selected, then the component continues at block 406, else the component continues at block 404. In block 404, the component invokes a generate inner 3D mesh component to generate, based on the selected 3D image, an inner 3D mesh representing the endocardial layer of the heart wall. In block 405, the component invokes a generate heart wall 3D mesh to generate, based on the selected 3D image, a heart wall 3D mesh indicating the inner layer and the outer layer of the heart wall. The component then loops to block 402 to select the next 3D image. In block 406, the component selects the next heart wall 3D mesh in time sequence. In decision block 407, if the penultimate heart wall mesh has already been selected, the component then completes, else the component continues at block 408. In block 408, the component selects the next intermediate time that is in between the start time, which is the time of the selected heart wall 3D mesh, and the end time, which is the time of the next heart wall 3D mesh. In decision block 409, if all the intermediate times have already been selected, then the component loops to block 406 to select the next heart wall 3D mesh, else the component continues at block 410. In block 410, the component invokes the generate intermediate 3D mesh component to generate an intermediate 3D mesh based on the selected heart wall 3D mesh and the next heart wall 3D mesh and the selected intermediate time. The component then loops to block 408 to select the next intermediate time. Alternatively, the 3D visualization system may generate an end 3D mesh based on a start 3D mesh or vice versa. One technique that generates a 3D mesh corresponding to systole based on a 3D mesh corresponding to diastole or vice versa is described in Beetz, M., Acero, J. C., Banerjee, A., Eitel, I., Zacur, E., Lange, T., Stiermaier, T., Evertz, R., Backhaus, S. J., Thiele, H. and Bueno-Orovio, A., 2022 September. Mesh U-Nets for 3D cardiac deformation modeling. In International Workshop on Statistical Atlases and Computational Models of the Heart (pp. 245-257). Cham: Springer Nature Switzerland, which is hereby incorporated by reference.

Although not illustrated the component may calculate various wall characteristics for the 3D meshes. For example, the component may calculate a heart wall thickness for the inner vertices of each 3D mesh. As another example, the component may calculate wall motion characteristics for pairs of 3D meshes such as those corresponding to maximum contraction and maximum expansion. The 3D visualization system may also allow a user to employ the user interface to select times within the cardiac cycle to dynamically calculate wall characteristics. For example, referring to FIG. 1, a user may select two times along the ECG and select that wall motion characteristics be calculated based on those times using the characteristics control.

Figure 8:
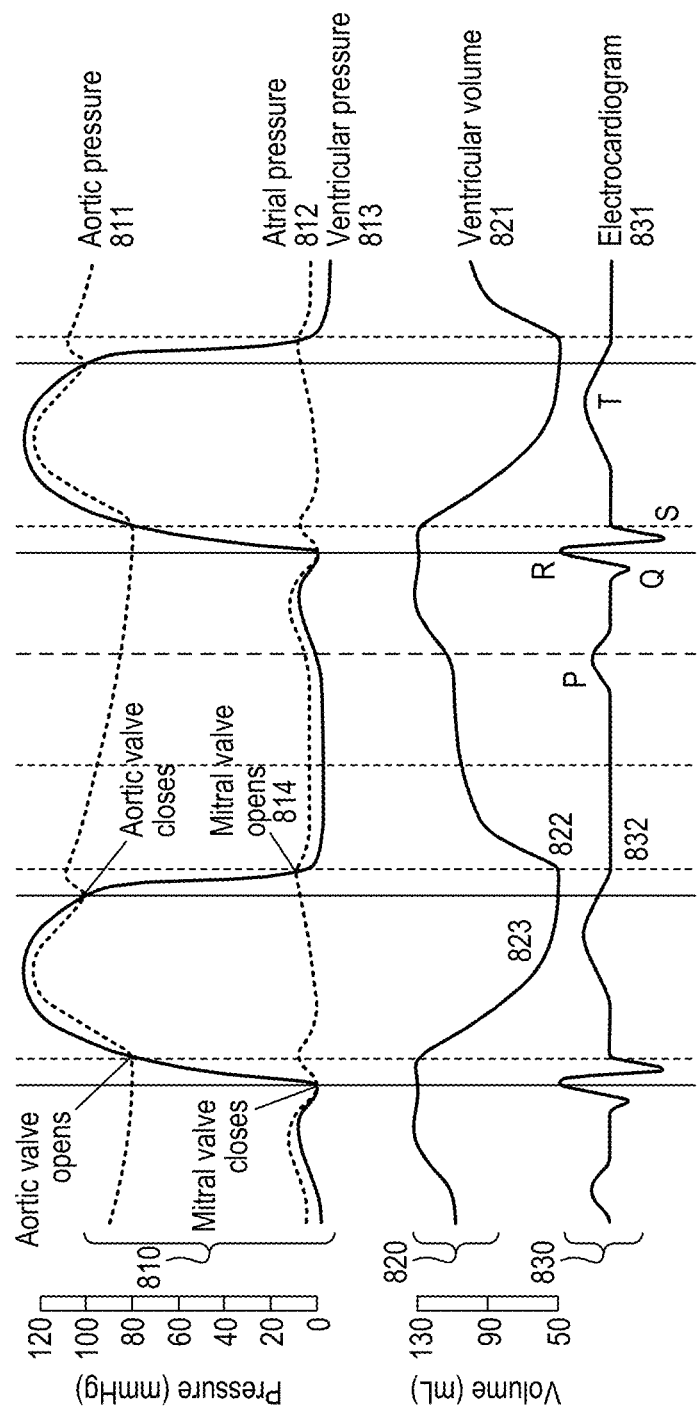
FIG. 8 illustrates a Wiggers diagram.

The 3D visualization system may employ mapping of a voltage-time series or pressure-time series to chamber volume when generating an intermediate 3D mesh. A Wiggers diagram is an example of such a mapping. FIG. 8 illustrates a Wiggers diagram. The upper portion 810 provides graph of aortic pressure 811, atrial pressure 812, and ventricular pressure 813 during a cardiac cycle. The middle portion 820 provides a graph 821 of ventricular volume during a cardiac cycle. The lower portion 830 provides a graph 831 of voltage during a cardiac cycle. As illustrated, the minimum ventricular volume 822 occurs at the pressure associated with the opening of the mitral valve 814 and voltage associated with the end of the T wave 832. As an example of the interpolation, if start time corresponds to the end of QRS complex and the end time corresponds to the end of the T wave, the interpolated ventricular volume 823 at the T peak would be approximately the same as (e.g., 95% of) the ventricular volume at the end of the T wave. In such a case, the 3D visualization system may set the location of each vertex of an intermediate 3D mesh to a location along a line from that vertex of the start 3D mesh to that vertex of the end 3D mesh that is much closer (e.g., 95% of the distance) to that vertex of the end 3D mesh. The 3D visualization system may also employ the mesh ML model, which factors in chamber volume, to generate the intermediate 3D mesh.

Figure 5:
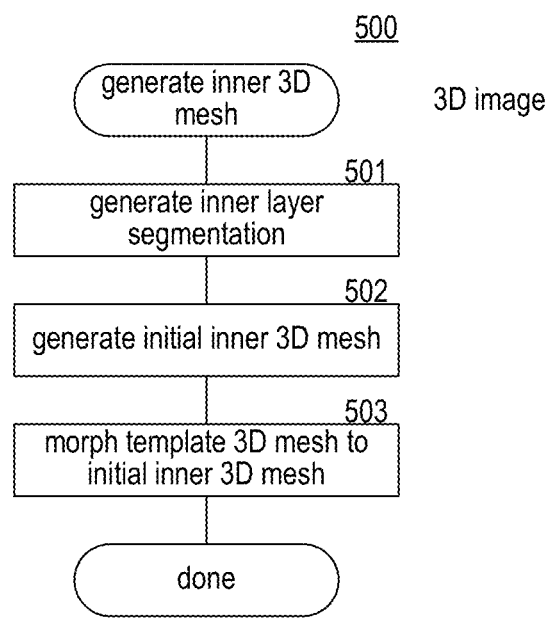
FIG. 5 is a flow diagram that illustrates processing of a generate inner 3D mesh component of the 3D visualization system in some embodiments.

FIG. 5 is a flow diagram that illustrates processing of a generate inner 3D mesh component of the 3D visualization system in some embodiments. The generate inner 3D mesh component 500 is invoked to generate, based on a 3D image, an inner 3D mesh with vertices corresponding to the inner layer of the heart wall. In block 501, the component generates an inner layer segmentation of the 3D image with vertices corresponding to location of the inner layers of the heart wall. A technique for segmentation is described in Kong, F., Wilson, N. and Shadden, S., 2021. A deep-learning approach for direct whole-heart mesh reconstruction. Medical image analysis, 74, p. 102222, which is hereby incorporated by reference. In block 502, the component generates an initial inner 3D mesh based on the inner layer segmentation. In block 503, the component generates an inner 3D mesh by morphing a template 3D mesh into the shape of the initial inner 3D mesh and then completes. A technique for generating a segmentation of a 3D image based on a U-Net ML model is described in Ronneberger, O., Fischer, P. and Brox, T., 2015. U-net: Convolutional networks for biomedical image segmentation. In Medical image computing and computer-assisted intervention-MICCAI 2015: 18th international conference, Munich, Germany, Oct. 5-9, 2015, proceedings, part III 18 (pp. 234-241). Springer International Publishing, which is hereby incorporated by reference. A technique for generating a 3D image based on a transformer architecture is described in Xiao, X., Dong, S., Yu, Y., Li, Y., Yang, G. and Qiu, Z., 2023. MAE-TransRNet: An improved transformer-ConvNet architecture with masked autoencoder for cardiac MRI registration. Frontiers in Medicine, 10, p. 1114571, which is hereby incorporated by reference. A technique for generating a 3D mesh from a segmented 3D image is described in Prassl, A. J., Kickinger, F., Ahammer, H., Grau, V., Schneider, J. E., Hofer, E., Vigmond, E. J., Trayanova, N. A. and Plank, G., 2009. Automatically Generated, Anatomically Accurate Meshes for Cardiac Electrophysiology Problems. IEEE Trans Biomed Eng, 56(5), p. 1318, which is hereby incorporated by reference. The 3D visualization system may employ the Shrinkwrap modifier of Blender to perform the morphing. Blender is open-source system that supports the generating, displaying, and rotating 3D graphics. (Blender Foundation, Blender, version 2.93, Blender, 2023. [Online]. Available: https://www.blender.org/.)

Figure 6:
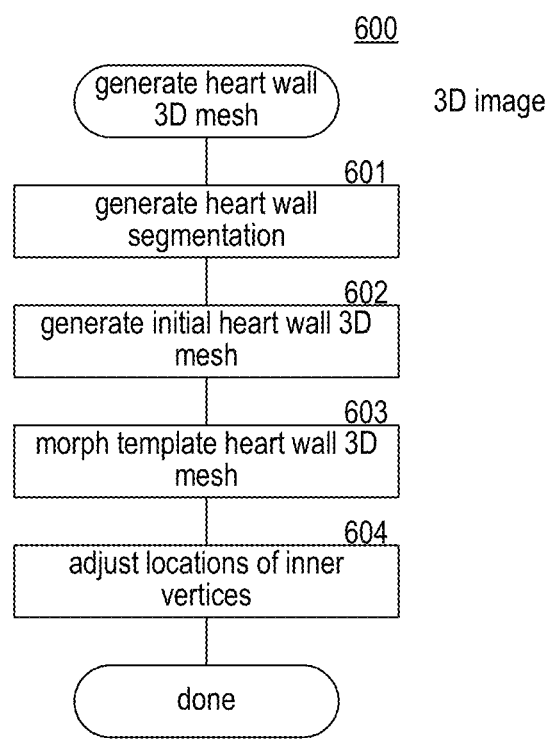
FIG. 6 is a flow diagram that illustrates the processing of a generate heart wall 3D mesh component in some embodiments.

FIG. 6 is a flow diagram that illustrates the processing of a generate heart wall 3D mesh component in some embodiments. The generate heart wall 3D mesh component 600 is invoked to generate a heart wall 3D mesh based on a 3D image. In block 601, the component generates a heart wall segmentation of the 3D image. In block 602, the component generates an initial heart wall 3D mesh based on the heart wall segmentation. In block 603, the component morphs a template heart wall 3D mesh to the geometry of the initial 3D mesh to generate the heart wall 3D mesh. In block 604, the component adjusts the locations of the inner vertices of the heart wall 3D mesh based on the locations of the vertices of the inner 3D mesh. The segmentation of the heart wall may not be as accurate as the segmentation of the inner layer by itself. The adjusting helps improve the accuracy of the locations associated with the vertices of the inner layer of the heart wall 3D mesh. The component then completes.

Figure 7:
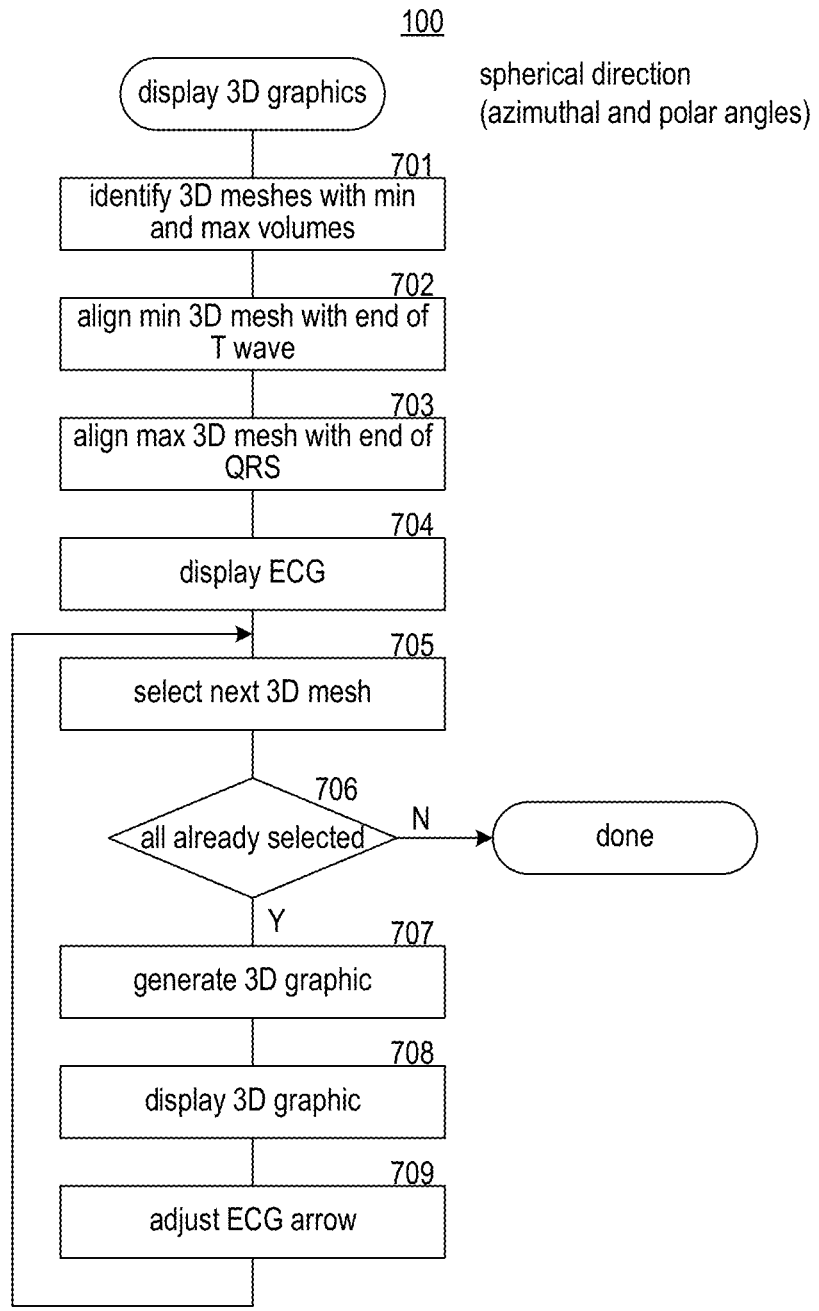
FIG. 7 is a flow diagram that illustrates the processing of a display 3D graphics component of the 3D visualization system in some embodiments.

FIG. 7 is a flow diagram that illustrates the processing of a display 3D graphics component of the 3D visualization system in some embodiments. The display 3D graphics component 700 displays a sequence of 3D graphics based on a sequence of 3D meshes. The 3D graphics may be displayed based on various parameters that a user may indicate using the user interface control. For example, the user may identify spherical direction (e.g., azimuthal angle and polar angle) from which the 3D graphic is to be viewed. In block 701, the component identifies 3D meshes with the minimum and maximum volumes. In block 702, the component aligns the 3D mesh with the minimum volume to the end of a T wave of the displayed ECG. In block 703, the component aligns the 3D mesh with the maximum volume to the end of the QRS segment. Alternatively, the component may employ the start times, intermediate times, and end times of the 3D meshes to align with the ECG. In block 704 the component displays an ECG that was collected during the collection of the 3D images. In block 705, the component selects the next 3D mesh. In decision block 706, if all the 3D meshes have already been selected, then the component completes, else the component continues at block 707. In block 707, the component generates a 3D graphic based on the 3D mesh. In block 708, the component displays the 3D graphic based on the parameters specified by the user. In block 709, the component adjusts the ECG arrow based on a time associated with the selected 3D mesh. The component then loops to block 705 to select the next 3D mesh. The 3D visualization system may employ the Blender open-source system to generate, display, and rotate the 3D graphic.

The component may alternatively generate a 3D graphic for each 3D mesh once (e.g., prior to displaying any 3D graphic). The component may also generate wall characteristics for vertices of the 3D meshes which can be indicated on the 3D graphics. For example, the indicators for heart wall strain may vary from red to blue with red representing high strain, green representing normal strain, and blue representing low strain. Different wall characteristics may be simultaneously represented on a 3D graphic. For example, heart wall strain may be represented using colors and heart wall thickness may represented using cross hatching. The source location of an arrhythmia may also be indicated on the 3D graphics.

An ML model employed by the 3D visualization system may be any of a variety or combination of supervised, semi-supervised, self-supervised, unsupervised, or reinforcement learning ML models including an NN such as a fully connected, convolutional, recurrent, or autoencoder NN (e.g., U-Net for segmentation or a convolutional neural network to the mesh ML model), K-means clustering (e.g., for determining wall characteristics), transformer, a generative adversarial network or a diffusion model (e.g., trained using 3D images of EHRs to generate additional training data such as 3D images), transformer (e.g., for segmentation), and so on. When the ML model is a deep neural network, the model is trained using training data that includes features derived from data and labels corresponding to the data. For example, the training data may be 3D images with a feature being the image itself, a segmentation of the image, and so on and the labels may be 3D meshes. The training results in a set of weights for the activation functions of the layers of the deep neural network. The trained deep neural network can then be applied to new data to generate a label for that new data. An ML model may generate values of discrete domain (e.g., classification), probabilities, and/or values of a continuous domain (e.g., regression value, classification probability).

Various techniques can be used to train a support vector machine such as adaptive boosting, which is an iterative process that runs multiple tests on a collection of training data. Adaptive boosting transforms a weak learning algorithm (an algorithm that performs at a level only slightly better than chance) into a strong learning algorithm (an algorithm that displays a low error rate). The weak learning algorithm is run on different subsets of the training data. The algorithm concentrates increasingly on those examples in which its predecessors tended to show mistakes. The algorithm corrects the errors made by earlier weak learners. The algorithm is adaptive because it adjusts to the error rates of its predecessors. Adaptive boosting combines rough and moderately inaccurate rules of thumb to create a high-performance algorithm. Adaptive boosting combines the results of each separately run test into a single, very accurate classifier. Adaptive boosting may use weak classifiers that are single-split trees with only two leaf nodes.

An NN has three major components: architecture, loss function, and search algorithm. The architecture defines the functional form relating the inputs to the outputs (in terms of network topology, unit connectivity, and activation functions). The search for a set of weights that minimizes the loss function is the training process. An NN model may use a radial basis function (RBF) network and a standard or stochastic gradient descent as the search technique with backpropagation.

A convolutional neural network (CNN) has multiple layers such as a convolutional layer, a rectified linear unit (ReLU) layer, a pooling layer, a fully connected (FC) layer, and so on. Some more complex CNNs may have multiple convolutional layers, pooling layers (e.g., 32 layers), and FC layers. Each layer includes a neuron for each output of that layer. A neuron inputs outputs of prior layers (or original input) and applies an activation function to the inputs to generate an output. Each neuron of a fully connected layer inputs all the outputs of the prior layer.

A convolutional layer may include multiple filters (also referred to as kernels or activation functions). A filter inputs a convolutional window, for example, of a 3D image, applies weights to each pixel of the convolutional window, and outputs value for that convolutional window. For example, if the 3D image is 2048 by 2048 pixels, the convolutional window may be 32 by 32 pixels. The filter may apply a different weight to each of the 1024 pixels in a convolutional window to generate the value. The convolutional layer may include, for each filter, a node (also referred to as a neuron) for each pixel of 3D image assuming a stride of one with appropriate padding. Each node outputs a feature value based on a set of weights for the filter that are learned.

An activation function has a weight for each input and generates an output by combining the inputs based on the weights. The activation function may be a ReLU that sums the values of each input times its weight to generate a weighted value and outputs max(0, weighted value) to ensure that the output is not negative. The weights of the activation functions are learned when training an ML model. The ReLU function of max(0,weighted value) may be represented as a separate ReLU layer with a neuron for each output of the prior layer that inputs that output and applies the ReLU function to generate a corresponding "rectified output."

A pooling layer may be used to reduce the size of the outputs of the prior layer by downsampling the outputs. For example, each neuron of a pooling layer may input 16 outputs of the prior layer and generate one output resulting in a 16-to-1 reduction in outputs.

An FC layer includes neurons that each input all the outputs of the prior layer and generate a weighted combination of those inputs. For example, if the penultimate layer generates 4096 outputs and the FC layer includes 2048 neurons, each neuron inputs the 4096 outputs and applies weights to generate a location (x, y, z) for each of 4096 vertices of a 3D mesh.

One example of a CNN is a U-Net ML model. The U-Net ML model includes a contracting path and an expansive path. The contracting path includes a series of max pooling layers to reduce spatial information of the input image and increase feature information. The expansive path includes a series of upsampling layers to convert the feature information to the output image. The input and output of a U-Net represent an image such as an image of patient ECG as input and an image of a base region as output.

The 3D visualization system may employ various ML model architectures for processing the various 3D meshes. In some embodiments, the 3D visualization system may employ a Graph Neural Network (GNN). A GNN is designed to operate on graph data based on convolutions over neighborhoods of nodes of the graph data. A 3D mesh can be viewed as a graph where vertices are nodes and edges are connections between these nodes. GNNs operate by passing messages between nodes (vertices) and aggregating information from neighbors. Weights for vertex-level features are learned based on both the individual properties of vertices and their relations to neighbors. (See, Gori, M., Monfardini, G. and Scarselli, F., 2005 July. A new model for learning in graph domains. In Proceedings. 2005 IEEE International Joint Conference on Neural Networks, 2005. (Vol. 2, pp. 729-734). IEEE, which is hereby incorporated by reference.) In some embodiments, different types of GNNs may be employed such as a Graph Attention Network, which implements an attention mechanism, or a Graph Convolutional Network, which implements convolutions. The training data may include a 3D mesh with each vertex has features and a label. The feature may include the location of a vertex and the label may be, for example, wall thickness for vertices representing the endocardium. When training a GNN, nodes send information to neighboring nodes based on a loss function to learn the weights for features of the nodes. After the GNN is trained, a 3D mesh (e.g., wall strain 3D mesh or tissue state 3D mesh) can be input to the GNN to generate a label for each node based on features of nodes of the 3D mesh.

A GNN processes a graph G=(V,E) that consists of nodes (vertices) V and edges E that connect pairs of nodes. Nodes and edges can have features that describe wall characteristics such as wall thickness and tissue state. GNNs typically operate through a mechanism known as message passing or neighborhood aggregation. In each layer of a GNN, nodes aggregate information (messages) from their neighbors. This aggregation helps nodes to learn about their local graph structure. Nodes can update their features by combining their own features with aggregated messages from their neighbors, often using NNs. Edges can also have features and play a role in how messages are passed and aggregated. A GNN layer may perform the following processing:

$$av(l+1)=\text{AGGREGATE}(l)(\{hu(l):u\in N(v)\})$$

$$hv(l+1)=\text{COMBINE}(l)(hv(l),av(l+1))$$

where hv(l) is the feature vector of node v at layer l, N(v) represents the neighbors of v, and av(l+1) is the aggregated information. Gradient descent may be employed to optimize the parameters of the aggregate and combine functions.

A generative adversarial network (GAN) may also be used to generate additional training data. (See, Goodfellow, I., Pouget-Abadie, J., Mirza, M., Xu, B., Warde-Farley, D., Ozair, S., Courville, A. and Bengio, Y., 2020. Generative adversarial networks. Communications of the ACM, 63(11), pp. 139-144, which is hereby incorporated by reference.) A GAN employs a generator and discriminator and is trained using training data such as 3D images of the 3D visualization system. The generator generates 3D images based on random input. The generator is trained with the goal of generating 3D images that cannot be distinguished from real 3D images. The discriminator indicates whether an input 3D image is real or generated. The generator and discriminator are trained in parallel to learn weights. The generator is trained to generate increasingly more realistic 3D images, and the discriminator is trained to discriminate between real 3D images and generate 3D images more effectively. After being trained, the generator can be used to generate 3D images that are realistic.

The 3D visualization system may employ a diffusion ML model to generate additional training data using a generative process. (See, Rombach, R., Blattmann, A., Lorenz, D., Esser, P. and Ommer, B., 2022. High-resolution image synthesis with latent diffusion models. In Proceedings of the IEEE/CVF conference on computer vision and pattern recognition (pp. 10684-10695), which is hereby incorporated by reference.) A diffusion ML model is a generative ML model that inputs noisy data and progressively denoises the data until the denoised data appears to be indistinguishable from real data such as a 3D image or 3D mesh with vertices indicating wall characteristics. In the case of vertices indicating wall characteristics, wall characteristics may input a conditioning data as described below. A diffusion ML model is trained using a forward diffusion process that successively adds noise to input training data such as 3D images to generate noisy data and a reverse diffusion process that successively denoises the noisy data to generate denoised data that approximates the input training data. The training learns weights for the reverse diffusion process that tend to minimize the difference between the input training data and the denoised data. After a diffusion model is trained, the 3D visualization system employs the reverse diffusion process to generate training data for an ML model. To do so, randomly generated noisy data is input to the reverse diffusion process which denoises the noisy data to generate the noised data that appears to real data.

The forward diffusion process employs a Markov chain that incrementally adds Gaussian noise to the training data over a series of steps. This process transforms the training data from its initial distribution to a Gaussian distribution. The reverse diffusion process employs an NN to incrementally approximate and remove the noise that was added at each step of the forward diffusion process. When generating data, randomly generated noisy data is input to the reverse diffusion process which incrementally removes the noise that was learned during training.

The forward diffusion process systematically adds Gaussian noise to the original data x0 Gaussian noise over T timesteps, resulting in a sequence of increasingly noisy data x1, x2, . . . , xT. The process at each time step t may be represented by the equation:

$$x_t = \sqrt{\alpha_t} x_{t-1} + \sqrt{1-\alpha_t} \epsilon_t, \epsilon_t \in N(0,I)$$

where $x_t$ is data at timestep t, $\epsilon_t$ is Gaussian noise, $\alpha_t$ is the amount of noise added, and I is the identity matrix.

The reverse diffusion process learns the distribution of the training data by starting from noise and progressively denoising it over the timesteps. The training estimates the reverse of the forward diffusion process using an NN that may be represented by the equation:

$$x_{t-1} = \frac{1}{\sqrt{\alpha_t}}\left(x_t - \frac{1-\alpha_t}{\sqrt{1-\overline{\alpha}_t}} f_\theta(x_t, t)\right)$$

where $\overline{\alpha}_t = \Pi_{i=1}^{t} \alpha_i$ represent the cumulative noise and $f_\theta(x_t,t)$ represents the NN.

The goal of training a diffusion model is to minimize the difference between the original data and the data reconstructed by the reverse diffusion process using a loss function that may be represented by the equation.

$$L(\theta) = E_{x_0, \epsilon_t, t}[\|\epsilon_t - f_\theta(x_t, t)\|^2].$$

A diffusion model may also include a conditioning mechanism that allows for factoring in a domain-specific information into the reverse diffusion process. The domain-specific information may be employed by a cross-attention mechanism of the NN (e.g., U-Net architecture) of the reverse diffusion process.

Transformer machine learning was introduced as an alternative to a recurrent neural network that is both more effective and more parallelizable. (See, Vaswani, A., Shazeer, N., Parmar, N., Uszkoreit, J., Jones, L., Gomez, A. N., Kaiser, Ł. and Polosukhin, I., 2017. Attention is all you need. Advances in neural information processing systems, 30, which is hereby incorporated by reference.) Transformer machine learning was originally described in the context of natural language processing (NLP) but has been adapted to other applications such as image processing to augment or replace a CNN. (See, Dosovitskiy, A., Beyer, L., Kolesnikov, A., Weissenborn, D., Zhai, X., Unterthiner, T., Dehghani, M., Minderer, M., Heigold, G., Gelly, S. and Uszkoreit, J., 2020. An image is worth 16×16 words: Transformers for image recognition at scale. arXiv preprint arXiv: 2010.11929, which is hereby incorporated by reference.)

A transformer includes an encoder whose output is input to a decoder. The encoder includes an input embedding layer followed by one or more encoder attention layers. The input embedding layer generates an embedding of the inputs. For example, if a transformer ML model is used to segment a 3D image, each pixel may be represented as a token that includes an embedding of its color or shading and its positional information.

The first encoder attention layer inputs the embeddings and the other encoder attention layers input the output from the prior encoder attention layer. An encoder attention layer includes a multi-head attention mechanism followed by a normalization sublayer whose output is input to a feedforward neural network followed by a normalization sublayer. A multi-head attention mechanism includes multiple self-attention mechanisms that each inputs the encodings of the previous layer and weighs the relevance encodings to other encodings. For example, the relevance may be determined by the following attention function:

$$\text{Attention}(Q, K, V) = \text{softmax}\left(\frac{QK^T}{\sqrt{d_k}}\right)V$$

where Q represents a query, K represents a key, V represents a value, and $d_k$ represents the dimensionality of K. This attention function is referred to as scaled dot-product attention. The query, key, and value of an encoder multi-head attention mechanism may be set to the input of the encoder attention layer. The multi-head attention mechanism determines the multi-head attention as represented by the following:

$$\text{MultiHead}(Q,K,V) = \text{concat}(\text{head}_1, \ldots, \text{head}_8)W_o$$

$$\text{head}_i = \text{Attention}(QW_i^Q, KW_i^K, VW_i^V)$$

where W represents weights that are learned during training. The weights for the feedforward networks are also learned during training. The weights may be initialized to random values. A normalization layer normalizes its input to a vector having a dimension as expected by the next layer or sublayer.

The decoder includes an output embedding layer, decoder attention layers, a linear layer, and a softmax layer. The output embedding layer inputs the output of the decoder shifted right. Each decoder attention layer inputs the output of the prior decoder attention layer (or the output embedding layer) and the output of the encoder. The embedding layer is input to the decoder attention layer, the output of the decoder attention layer is input the linear layer, and the output of the linear layer is input to the softmax layer which outputs probabilities. A decoder attention layer includes a decoder masked multi-head attention mechanism followed by a normalization sublayer, a decoder multi-head attention mechanism followed by a normalization sublayer, and a feedforward neural network followed by a normalization sublayer. The decoder masked multi-head attention mechanism masks the input so that predictions for a position are only based on outputs for prior positions. A decoder multi-head attention mechanism inputs the normalized output of the decoder masked multi-head attention mechanism as a query and the output of the encoder as a key and a value. The feedforward neural network inputs the normalized output of the decoder multi-head attention mechanism. The normalized output of the feedforward neural network is the output of that multi-head attention layer. The weights of the linear layer are also learned during training.

The 3D visualization system may employ various techniques to identify features (e.g., of a 3D image) to be employed by an ML model. For example, the features used to train a wall strain ML model may be vertices corresponding to the endocardium and the epicardium. The features used by an ML model may be manually or automatically selected. An assessment of which features may be useful in providing an accurate output for a ML model are referred to as informative feature. The assessment of which features are informative may be based on various feature selection techniques such as a predictive power score, a lasso regression, a mutual information analysis, and so on.

The features may also be latent vectors generated using an ML model such as a VAE. For example, a variational autoencoder may be trained using 3D images or 3D meshes. When a 3D image or a 3D mesh is input into the trained VAE, the latent vector that is generated is a feature vector that represents the 3D image or the 3D mesh. That feature vector can be input into another trained ML model such as a neural network to generate an output. When training a mesh ML model, for example, to generate a 3D mesh given a 3D image, the training 3D images are input to the VAE to generate training feature vectors that can then be labeled with a 3D mesh. The mesh ML model is then trained using the labeled feature vectors. The VAE may be trained independently of the mesh 3D model. Alternatively, the encoder of the VAE that generates the latent vector (and not the decoder) may be trained in parallel with the mesh ML model using a combined loss function. In such a case, no autoencoding is performed. Rather the latent vector represents features of a 3D image that are particularly relevant to generating 3D meshes.

The following paragraphs describe various aspects of the 3D visualization system. An implementation of the visualization system may employ any combination or sub-combination of the aspects and may employ additional aspects. The processing of the aspects may be performed by one or more computing systems with one or more processors that execute computer-executable instructions that implement the aspects and that are stored on one or more computer-readable storage mediums.

In some aspects, the techniques described herein relate to a method performed by one or more computing systems, the method including: accessing a start three-dimensional (3D) image of a heart of a patient associated with a start time and an end 3D image of the heart of the patient associated with an end time; for each of the start 3D image and the end 3D image, generating a heart wall segmentation of that 3D image that identifies the inner layer and the outer layer of the heart wall; generating, based on the heart wall segmentation, a heart wall 3D mesh representing geometry of the heart wall with vertices representing locations on an inner layer and locations on an outer layer; and assigning characteristic values to vertices of the heart wall 3D mesh, the characteristic values indication a characteristic the heart wall; for each of one or more intermediate times between the start time and the end time, generating an intermediate heart wall 3D mesh that has a heart wall geometry is an interpolation of the geometries of the start heart wall 3D mesh and the end heart wall 3D mesh; and assigning characteristic values to the vertices of the intermediate heart wall 3D mesh; and displaying a representation of the start heart wall 3D mesh, the one or more intermediate heart wall 3D mesh, and the end heart wall 3D mesh, the representations including indications of the characteristic values derived from the characteristic values of the start heart wall 3D mesh and the end heart wall 3D mesh. In some aspects, the techniques described herein relate to a method wherein the representations are displayed in sequence. In some aspects, the techniques described herein relate to a method further including displaying a representation of an electrocardiogram corresponding to a least a portion of a cardiac cycle encompassing the start time and the end time. In some aspects, the techniques described herein relate to a method wherein the characteristic is related to source location of an arrhythmia source, heart wall thickness, heart wall strain, heart wall strain rate, heart wall conduction velocity, tissue state, voltage, or electrical activation.

In some aspects, the techniques described herein relate to a method performed by one or more computing systems, the method including: accessing a start three-dimensional (3D) image of the heart of a patient associated with a start indicator; accessing an end 3D image of the heart of the patient associated with an end indicator; generating a start heart wall 3D mesh representing a start geometry of the heart wall that is derived from a segmentation of the start 3D image, the start heart wall 3D mesh having vertices, one or more of the vertices are each associated with a start characteristic value; generating an end heart wall 3D mesh representing an end geometry of the heart wall that is derived from a segmentation of the end 3D image, the end heart wall 3D mesh having vertices, one or more of the vertices are each associated with an end characteristic value; generating an intermediate heart wall 3D mesh that is associated with an intermediate indicator, that represents an intermediate geometry of the heart wall that is an interpolation based on the start geometry and the end geometry factoring in the start indicator, the intermediate indicator, and the end indicator, and that has vertices, one or more of the vertices is each associated with an intermediate characteristic value; and displaying 3D graphics derived from the start heart wall 3D mesh, the intermediate heart wall 3D mesh, and the end heart wall 3D mesh. In some aspects, the techniques described herein relate to a method wherein the start indicator, the intermediate indicator, and the end indicator are times. In some aspects, the techniques described herein relate to a method wherein the start indicator, the intermediate indicator, and the end indicator are landmarks of an electrocardiogram. In some aspects, the techniques described herein relate to a method wherein the start indicator, the intermediate indicator, and the end indicator are times and the heart wall 3D meshes are displayed in sequence based on time. In some aspects, the techniques described herein relate to a method further including displaying an electrocardiogram collected while the start 3D image and the end 3D image are collected.

In some aspects, the techniques described herein relate to one or more computing systems including: one or more computer-readable storage mediums that store computer-executable instructions for controlling the one or more computing systems to: access a first heart wall three-dimensional (3D) mesh that represents a first geometry of a heart wall derived from a first heart wall 3D image of a heart and that is associated with a first indicator; generate a second heart wall 3D mesh that represents a second geometry of the heart wall that is based on the first geometry, a second indicator, and a first volume associated with the first heart wall 3D mesh and a second volume associated with the second heart wall 3D mesh; and display in sequence representations the first heart wall 3D mesh and the second 3D heart wall mesh; and one or more processors for controlling the one or more computing systems to execute one or more of the computer-executable instructions. In some aspects, the techniques described herein relate to one or more computing systems wherein the first indicator is a first time with a cardiac cycle and the second indicator is a second time within the cardiac cycle, and wherein the second volume is derived from a mapping of time within a cardiac cycle to chamber volume. In some aspects, the techniques described herein relate to one or more computing systems wherein a plurality of second heart wall 3D meshes are generated for different second indicators and the computer-executable instructions further include instructions to display in the sequence representations of the plurality of second heart wall 3D meshes. In some aspects, the techniques described herein relate to one or more computing systems wherein the second heart wall 3D mesh is generated further based on a third heart wall 3D mesh that represents a third geometry of the heart wall derived from a third 3D image of the heart and that is associated with a third indicator. In some aspects, the techniques described herein relate to one or more computing systems wherein first indicator represents a first time within a cardiac cycle, the second indicator represents a second time within the cardiac cycle, and the third indicator represents a third time within the cardiac cycle and wherein the second time is in between the first time and the third time. In some aspects, the techniques described herein relate to one or more computing systems wherein first indicator represents a first time within a cardiac cycle, the second indicator represents a second time within the cardiac cycle, and the third indicator represents a third time within the cardiac cycle and wherein the second time is not between the first time and the third time. In some aspects, the techniques described herein relate to one or more computing systems wherein the first indicator represents a first time within a cardiac cycle, the second indicator represents a second time within the cardiac cycle, and the third indicator represents a third time within the cardiac cycle and wherein the second time is in between the first time and the third time and wherein the computer-executable instructions further include instructions to generate plurality of second heart wall 3D meshes for different second times and to display in the sequence representations of the plurality of second heart wall 3D meshes. In some aspects, the techniques described herein relate to one or more computing systems wherein the computer-executable instructions include instructions that display an electrocardiogram of a cardiac cycle. In some aspects, the techniques described herein relate to one or more computing systems wherein the first 3D image and the third 3D images are collected during the cardiac cycle. In some aspects, the techniques described herein relate to one or more computing systems wherein the computer-executable instructions include instructions to display a cycle time indicator in association with the displayed electrocardiogram to indicate the times associated with the 3D meshes as their representations are displayed. In some aspects, the techniques described herein relate to one or more computing systems wherein each heart wall 3D mesh includes vertices corresponding to an inner layer and an outer layer of the heart wall. In some aspects, the techniques described herein relate to one or more computing systems wherein the displayed representations provide a slice view that illustrates the inner layer, a myocardial layer, and the outer layer of a heart wall.

In some aspects, the techniques described herein relate to one or more computing systems including: one or more computer-readable storage mediums that store computer-executable instructions for controlling the one or more computing systems to: generate a start heart wall 3D mesh representing a start geometry of a heart wall, the start heart wall 3D mesh having vertices, one or more of the vertices are each associated with a start characteristic value of a characteristic; generate an end heart wall 3D mesh representing an end geometry of the heart wall, the end heart wall 3D mesh having vertices, one or more of the vertices are each associated with an end characteristic value; generate intermediate heart wall 3D meshes that each represents an intermediate geometry of the heart wall, each intermediate heart wall 3D mesh having vertices, one or more of the vertices of a heart wall 3D mesh is each associated with an intermediate characteristic value; and display 3D graphics derived from the heart wall 3D meshes wherein the 3D graphics are displayed in sequence based on a time associated with each heart wall 3D mesh; and one or more processors for controlling the one or more computing systems to execute one or more of the computer-executable instructions. In some aspects, the techniques described herein relate to one or more computing systems wherein the intermediate heart wall 3D meshes are derived from the start heart wall 3D mesh and the end heart wall 3D mesh. In some aspects, the techniques described herein relate to one or more computing systems wherein the geometries of the heart wall 3D meshes are based on a simulation of motion of the heart wall. In some aspects, the techniques described herein relate to one or more computing systems wherein the simulation simulates electrical activity of a heart. In some aspects, the techniques described herein relate to one or more computing systems wherein the computer-executable instructions further include instructions to access a collection of simulation data derived from simulations of electrical activity of a heart, the simulated data for a simulation including simulated heart wall 3D meshes representing geometries of a heart wall during the simulation of electrical activity of a heart and including a simulated electrocardiogram derived from the simulated electrical activity and the start heart wall 3D mesh, the intermediate heart wall 3D meshes, and the end heart wall 3D mesh are simulated heart wall 3D meshes. In some aspects, the techniques described herein relate to one or more computing systems wherein the computer-executable instructions further include instructions to access a patient electrocardiogram and identify a simulated electrocardiogram derived from a simulation is similar to the patient electrocardiogram based on a similarity criterion and wherein the start heart wall 3D mesh, the intermediate 3D heart wall meshes, and the end heart wall 3D mesh are based on the simulated heart wall 3D meshes of the identified simulated simulation. In some aspects, the techniques described herein relate to one or more computing systems wherein the start heart wall 3D mesh and the end heart wall 3D mesh are derived from a simulation of electrical activity of a heart, wherein the simulation is based on a source location of an arrhythmia that is associated with a simulated heart wall 3D mesh, wherein the source location is associated with corresponding vertices of the start heart wall 3D mesh, the intermediate heart wall 3D meshes, and the end heart wall 3D mesh, and wherein the source location is indicated on the displayed 3D graphics. In some aspects, the techniques described herein relate to one or computing systems wherein the computer-executable instructions further include instructions to receive a user indication to rotate the display of the heart wall 3D meshes around a specified axis of rotation. In some aspects, the techniques described herein relate to one or more computing system wherein the computer-executable instructions further include instructions to display indications of the characteristic values of one or more characteristics associated with the 3D meshes, the characteristics including one or more of source location of an arrhythmia source, heart wall thickness, heart wall strain, heart wall strain rate, heart wall conduction velocity, tissue state, voltage, and electrical activation timing.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims.

We claim:

1. One or more computing systems comprising:
   one or more computer-readable storage mediums that store computer-executable instructions for controlling the one or more computing systems to:

access a first heart wall three-dimensional (3D) mesh that represents a first geometry of a heart wall derived from a first heart wall 3D image of a heart and that is associated with a first indicator;

generate a second heart wall 3D mesh that represents a second geometry of the heart wall that is based on the first geometry, a second indicator, and a first volume associated with the first heart wall 3D mesh and a second volume associated with the second heart wall 3D mesh; and display in sequence representations the first heart wall 3D mesh and the second 3D heart wall mesh;

wherein the second heart wall 3D mesh is generated further based on a third heart wall 3D mesh that represents a third geometry of the heart wall derived from a third 3D image of the heart and that is associated with a third indicator and one or more processors for controlling the one or more computing systems to execute one or more of the computer-executable instructions.

2. The one or more computing systems of claim 1 wherein the first indicator is a first time with a cardiac cycle and the second indicator is a second time within the cardiac cycle, and wherein the second volume is derived from a mapping of time within a cardiac cycle to chamber volume.

3. The one or more computing systems of claim 1 wherein a plurality of second heart wall 3D meshes are generated for different second indicators and the computer-executable instructions further include instructions to display in the sequence representations of the plurality of second heart wall 3D meshes.

4. The one or more computing systems of claim 1 wherein first indicator represents a first time within a cardiac cycle, the second indicator represents a second time within the cardiac cycle, and the third indicator represents a third time within the cardiac cycle and wherein the second time is in between the first time and the third time.

5. The one or more computing systems of claim 1 wherein first indicator represents a first time within a cardiac cycle, the second indicator represents a second time within the cardiac cycle, and the third indicator represents a third time within the cardiac cycle and wherein the second time is not between the first time and the third time.

6. The one or more computing systems of claim 1 wherein the first indicator represents a first time within a cardiac cycle, the second indicator represents a second time within the cardiac cycle, and the third indicator represents a third time within the cardiac cycle and wherein the second time is in between the first time and the third time and wherein the computer-executable instructions further include instructions to generate plurality of second heart wall 3D meshes for different second times and to display in the sequence representations of the plurality of second heart wall 3D meshes.

7. The one or more computing systems of claim 6 wherein the computer-executable instructions include instructions that display an electrocardiogram of a cardiac cycle.

8. The one or more computing systems of claim 7 wherein the first 3D image and the third 3D images are collected during the cardiac cycle.

9. The one or more computing systems of claim 8 wherein the computer-executable instructions include instructions to display a cycle time indicator in association with the displayed electrocardiogram to indicate the times associated with the 3D meshes as their representations are displayed.

10. The one or more computing systems of claim 1 wherein each heart wall 3D mesh includes vertices corresponding to an inner layer and an outer layer of the heart wall.

11. The one or more computing systems of claim 10 wherein the displayed representations provide a slice view that illustrates the inner layer, a myocardial layer, and the outer layer of a heart wall.

12. One or more computing systems comprising:
one or more computer-readable storage mediums that store computer-executable instructions for controlling the one or more computing systems to:
generate a start heart wall 3D mesh representing a start geometry of a heart wall, the start heart wall 3D mesh having vertices, one or more of the vertices are each associated with a start characteristic value of a characteristic;
generate an end heart wall 3D mesh representing an end geometry of the heart wall, the end heart wall 3D mesh having vertices, one or more of the vertices are each associated with an end characteristic value;
generate intermediate heart wall 3D meshes that each represents an intermediate geometry of the heart wall, each intermediate heart wall 3D mesh having vertices, one or more of the vertices of a heart wall 3D mesh is each associated with an intermediate characteristic value; and
display 3D graphics derived from the heart wall 3D meshes wherein the 3D graphics are displayed in sequence based on a time associated with each heart wall 3D mesh;
wherein the start heart wall 3D mesh and the end heart wall 3D mesh are derived from a simulation of electrical activity of a heart, wherein the simulation is based on a source location of an arrhythmia that is associated with a simulated heart wall 3D mesh, wherein the source location is associated with corresponding vertices of the start heart wall 3D mesh, the intermediate heart wall 3D meshes, and the end heart wall 3D mesh, and wherein the source location is indicated on the displayed 3D graphics and
one or more processors for controlling the one or more computing systems to execute one or more of the computer-executable instructions.

13. One or more computing systems comprising:
one or more computer-readable storage mediums that store computer-executable instructions for controlling the one or more computing systems to:
generate a start heart wall 3D mesh representing a start geometry of a heart wall, the start heart wall 3D mesh having vertices, one or more of the vertices are each associated with a start characteristic value of a characteristic;
generate an end heart wall 3D mesh representing an end geometry of the heart wall, the end heart wall 3D mesh having vertices, one or more of the vertices are each associated with an end characteristic value;
generate intermediate heart wall 3D meshes that each represents an intermediate geometry of the heart wall, each intermediate heart wall 3D mesh having vertices, one or more of the vertices of a heart wall 3D mesh is each associated with an intermediate characteristic value; and
display 3D graphics derived from the heart wall 3D meshes wherein the 3D graphics are displayed in sequence based on a time associated with each heart wall 3D mesh;

wherein the computer-executable instructions further include instructions to receive a user indication to rotate the display of the heart wall 3D meshes around a specified axis of rotation and one or more processors for controlling the one or more computing systems to execute one or more of the computer-executable instructions.

14. The one or more computing systems of claim 13 wherein the intermediate heart wall 3D meshes are derived from the start heart wall 3D mesh and the end heart wall 3D mesh.

15. The one or more computing systems of claim 13 wherein geometries of the heart wall 3D meshes are based on a simulation of motion of the heart wall.

16. The one or more computing systems of claim 15 wherein the simulation simulates electrical activity of a heart.

17. The one or more computing systems of claim 13 wherein the computer-executable instructions further include instructions to access a collection of simulation data derived from simulations of electrical activity of a heart, the simulated data for a simulation including simulated heart wall 3D meshes representing geometries of a heart wall during the simulation of electrical activity of a heart and including a simulated electrocardiogram derived from the simulated electrical activity and the start heart wall 3D mesh, the intermediate heart wall 3D meshes, and the end heart wall 3D mesh are simulated heart wall 3D meshes.

18. The one or more computing systems of claim 17 wherein the computer-executable instructions further include instructions to access a patient electrocardiogram and identify a simulated electrocardiogram derived from a simulation is similar to the patient electrocardiogram based on a similarity criterion and wherein the start heart wall 3D mesh, the intermediate 3D heart wall meshes, and the end heart wall 3D mesh are based on the simulated heart wall 3D meshes of the identified simulated simulation.

19. One or more computing systems comprising:
one or more computer-readable storage mediums that store computer-executable instructions for controlling the one or more computing systems to:
  generate a start heart wall 3D mesh representing a start geometry of a heart wall, the start heart wall 3D mesh having vertices, one or more of the vertices are each associated with a start characteristic value of a characteristic;
  generate an end heart wall 3D mesh representing an end geometry of the heart wall, the end heart wall 3D mesh having vertices, one or more of the vertices are each associated with an end characteristic value;
  generate intermediate heart wall 3D meshes that each represents an intermediate geometry of the heart wall, each intermediate heart wall 3D mesh having vertices, one or more of the vertices of a heart wall 3D mesh is each associated with an intermediate characteristic value; and
  display 3D graphics derived from the heart wall 3D meshes wherein the 3D graphics are displayed in sequence based on a time associated with each heart wall 3D mesh;
  wherein the computer-executable instructions further include instructions to display indications of the characteristic values of one or more characteristics associated with the 3D meshes, the characteristics including one or more of source location of an arrhythmia source, heart wall thickness, heart wall strain, heart wall strain rate, heart wall conduction velocity, tissue state, voltage, and electrical activation timing and
one or more processors for controlling the one or more computing systems to execute one or more of the computer-executable instructions.

* * * * *